(12) United States Patent
Rettich et al.

(10) Patent No.: US 7,670,357 B2
(45) Date of Patent: Mar. 2, 2010

(54) SURGICAL INSTRUMENT FOR MANIPULATING A BENT WIRE

(75) Inventors: Jürgen Rettich, Mühlheim (DE); Ingo Lederer, Kirchzarten (DE); Manfred Schmuck, Mühlheim-Stetten (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 554 days.

(21) Appl. No.: 11/179,119

(22) Filed: Jul. 12, 2005

(65) Prior Publication Data

US 2006/0009781 A1 Jan. 12, 2006

(30) Foreign Application Priority Data

Jul. 12, 2004 (DE) ........................ 10 2004 033 633

(51) Int. Cl.
*A61B 17/00* (2006.01)
(52) U.S. Cl. ..................................... 606/205
(58) Field of Classification Search ......... 606/205–209, 606/86 B, 281, 915, 101, 103
See application file for complete search history.

(56) References Cited

U.S. PATENT DOCUMENTS

| 2,578,506 | A | * | 12/1951 | Carnes, Jr. ................. 29/278 |
| 3,654,647 | A |   | 4/1972  | Neff |
| 3,861,430 | A | * | 1/1975  | Story ........................ 140/106 |
| 4,219,919 | A |   | 9/1980  | Fischbein et al. |
| 5,084,935 | A | * | 2/1992  | Kalthoff ...................... 7/132 |
| 5,139,498 | A | * | 8/1992  | Astudillo Ley ............. 606/69 |
| 5,156,609 | A | * | 10/1992 | Nakao et al. ............... 606/142 |
| 5,314,431 | A |   | 5/1994  | Graziano |
| 6,872,210 | B2| * | 3/2005  | Hearn ......................... 606/71 |

FOREIGN PATENT DOCUMENTS

| DE | 1956547     | 5/1971 |
| DE | 4329220     | 3/1995 |
| DE | 299 00 616 U1 | 4/1999 |
| EP | 0612505     | 1/1993 |
| WO | WO98/11838  | 3/1998 |

OTHER PUBLICATIONS

United Kingdom Search Report, GB0513072.9, Nov. 14, 2005.

* cited by examiner

*Primary Examiner*—(Jackie) Tan-Uyen T. Ho
*Assistant Examiner*—Gregory Anderson
(74) *Attorney, Agent, or Firm*—Howard & Howard Attorneys PLLC (57) ABSTRACT

What is described is a surgical instrument for manipulating a bent surgical wire. The surgical instrument is particularly suitable for inserting one or both ends of a wire, which is bent in the shape of a U, in apertures provided for that purpose in a bone plate. The instrument possesses two jaws that can be moved relative to one another for the purpose of generating a gripping force, at least one of the jaws having a wire-receiving device which positions a bent wire, which is to be received, in a plane substantially parallel to the direction of gripping force.

16 Claims, 6 Drawing Sheets

SURGICAL INSTRUMENT FOR MANIPULATING A BENT WIRE

FIELD OF THE INVENTION

The invention relates to a surgical instrument. More specifically, the invention relates to a surgical instrument for manipulating a bent surgical wire in the course of a surgical intervention.

BACKGROUND OF THE INVENTION

Surgical wires such as Kirschner wires (or "K-wires") are frequently used for fixing fragments of bone in position. For this purpose, in a first step a hole is usually drilled in a bone and/or in the fragment of bone to be fixed in position. In a second step, the wire is guided through the hole or holes.

The fractures often have to be additionally provided with a bone plate. In such a case, it is expedient to insert the surgical wire, through a first wire-receiving aperture in the bone plate, in the drilled hole formed in the bone (and/or in the fragment of bone). In addition, it is then also frequently necessary to cut off the surgical wire, bend it over and introduce the bent-over end of the wire through a second wire-receiving aperture in the bone plate. For this purpose, various instruments such as cutting forceps, bending forceps, etc. are used for manipulating the wire.

A pair of bending forceps for surgical operations which has two jaws that can be moved relative to one another is known from DE 1 956 547. On one of the two jaws, a substantially semicircular bending nose is provided. Said bending nose allows to bend the end of a surgical wire, which has been received between the jaws, in two steps by a total of 180°.

EP 0 612 505 A1 teaches a surgical instrument with the aid of which surgical clips can be fastened round a blood vessel for the purpose of tying it off. Said instrument possesses two jaws which can be moved relative to one another and between which the clips to be fastened are received.

A circular force-distributing plate with two apertures for the passing-through of a wire loop is known from WO 98/11838 A.

DE 43 29 220 A1 discloses a pair of medical wire forceps for bending and cutting-off the ends of wires.

The object underlying the invention is to indicate a surgical instrument for improved manipulation of a bent surgical wire.

BRIEF SUMMARY OF THE INVENTION

This object is achieved by means of a surgical instrument for manipulating a bent surgical wire, the instrument having two jaws that can be moved relative to one another for the purpose of generating a gripping (or clamping) force, wherein at least one of said jaws has a wire-receiving device which positions a bent wire, which is to be received, in a plane which is substantially parallel to the direction of the gripping force, wherein the at least one wire-receiving device is constructed as a groove or slot, and wherein said groove or slot is provided at a free end of the appertaining jaw and is defined by two side walls which stabilise the location of the bent wire and each extend in the plane which is substantially parallel to the direction of the gripping force.

The wire may be bent in such a way that it extends substantially within one plane (in the following referred to as the "wire plane"). Thus, for example, wires which are bent in the shape of a U, an L or a V define such a wire plane. By means of the wire-receiving device, the wire can be stabilised with respect to the jaws, preferably in such a way that the direction of the gripping force extends substantially parallel to the wire plane. Such an arrangement of the wire plane is expedient in order, in the case of a bent wire with two ends which has been received, to vary the distance between the two ends of the wire by actuating the instrument. According to an alternative embodiment, the instrument is constructed in such a way that the wire-receiving device is fixing the distance of the two ends of the wire relative to one another.

The wire-receiving device may extend substantially parallel to the direction of the gripping force. This means, in the case of a wire-receiving device which is constructed, for example, substantially in the form of a groove or slot, that said slot runs parallel to the direction of the gripping force.

The wire-receiving device is expediently open in the direction of a free end of the jaw. However, it would also be conceivably possible for said wire-receiving device to have an aperture which is constructed laterally on one of the jaws.

The wire-receiving device may have dimensions which are adapted to the shape of the bent wire to be received. In the case of a wire which is to be received and which is bent, for example, in the shape of a U or a V, the wire-receiving device may be contoured (at least in certain sections) in the shape of a U or a V.

The wire-receiving device may be provided on a single jaw. However, it would also be conceivably possible for said wire-receiving device to extend over both jaws. It may then be disposed symmetrically with respect to a plane perpendicular to the direction of the gripping force.

In addition to the wire-receiving device, the instrument may have a wire-bending device. Said wire-bending device may comprise a bending ram constructed in a region of a first of the two jaws, and a bending die constructed in a region of a second of the two jaws.

The wire-bending device may be constructed for the purpose of bending a wire in the shape of a U, an L or a V. However, it is also possible to provide a wire-bending device which forms simpler or more complex bent shapes.

According to one advantageous embodiment, the wire-bending device is designed for the purpose of forming a predefined radius of bending. In this case, the wire-receiving device may be dimensioned in conformity with said predefined radius of bending.

Besides the wire-receiving device, the surgical instrument may be provided with a wire-cutting device (optionally in addition to the wire-bending device). According to a first embodiment, said wire-cutting device may comprise two cutting edges which interact and which are each constructed on one of the two jaws. According to a second embodiment, the wire-cutting device comprises a cutting edge, which is disposed in a region of a first of the two jaws, and a wire-holding device in a region of the second jaw. Said wire-holding device is constructed so as to immobilise, with respect to the cutting edge, a wire which is to be cut to length.

The two jaws of the surgical instrument may be capable of swivelling relative to one another or capable of translatory movement relative to one another. According to one simple embodiment, the instrument is constructed in the form of forceps. However, more complex embodiments of the instrument are also possible which comprise a mechanism for a translatory movement of at least one of the two jaws.

According to a further aspect of the invention, a surgical system is provided which possesses, besides the surgical instrument, a bone plate with two wire-receiving apertures which are spaced apart from one another. The distance between said two receiving apertures may be selected in conformity with the dimensioning of the wire-receiving device and/or the dimensioning of the wire-bending device.

The surgical system may further comprise a bent wire whose radius of bending approximately corresponds to half the distance of the two wire-receiving apertures from one another.

BRIEF DESCRIPTION OF THE DRAWINGS

Further details and advantages of the invention emerge from the following description of a preferred exemplified embodiment of the invention, and also from the figures, of which.

DESCRIPTION OF A PREFERRED EMBODIMENT

A first embodiment of a surgical instrument constructed in the form of forceps will be described by way of an example below with reference to FIGS. 1 to 4 and 6. However, the invention could also be employed in instruments other than ones in the form of forceps. It should also be pointed out that the advantageous embodiment discussed below combines the three manipulative functions of wire-cutting, wire-bending and wire-positioning with one another. However, other embodiments of the invention might merely have the wire-positioning function (optionally in combination with the bending or cutting function). Moreover, the invention is not restricted to the manipulation of wires which are bent in the shape of a U.

Figure 1:
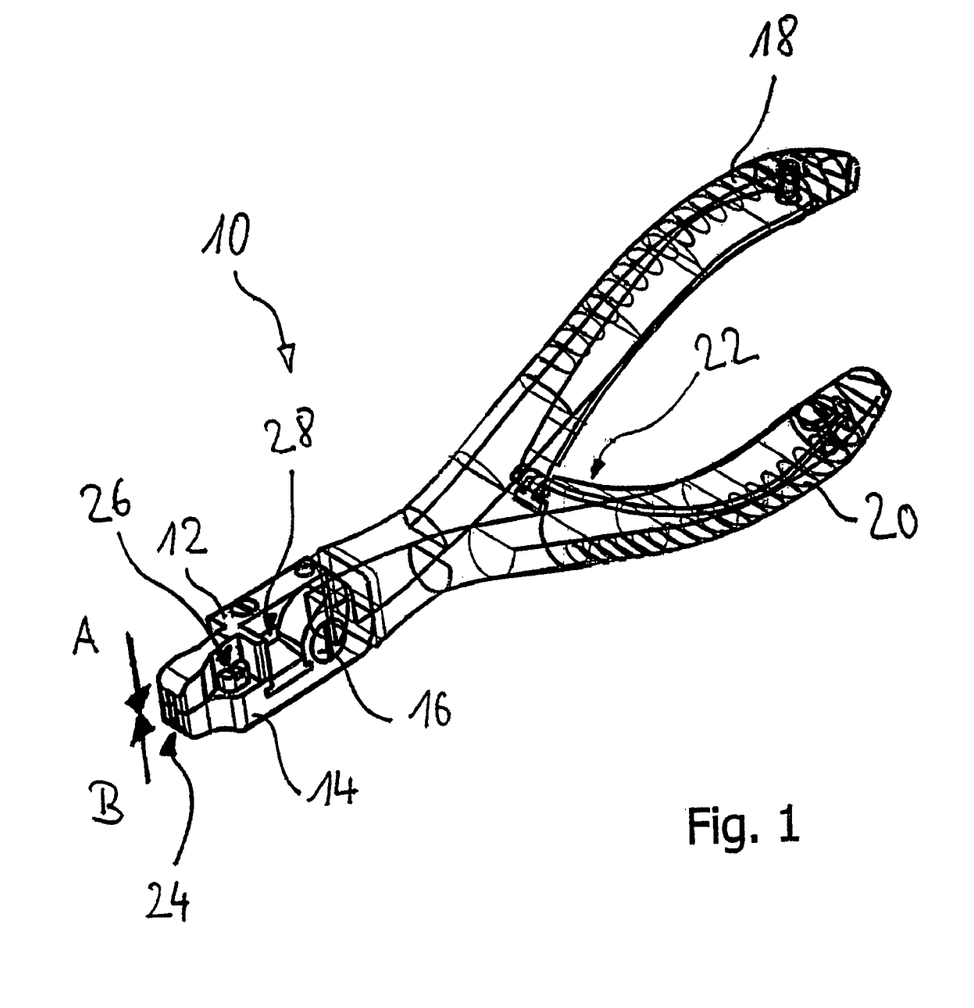
FIG. 1 shows a perspective view of a surgical instrument according to the invention.

FIG. 1 shows a perspective overall view of the surgical instrument 10 according to the invention for manipulating a bent surgical wire. In the example, said instrument 10 is constructed in the form of forceps and comprises two jaws 12, 14 which are capable of swivelling, relative to one another, with respect to a common bearing 16. The two jaws 12, 14 are each connected in one piece to a handle part 18, 20.

Said handle parts 18, 20 are coupled to one another by means of a spring mechanism 22. When actuation takes place, said spring mechanism 22 acts on the two handle parts 18, 20 in such a way that the two jaws 12, 14 of the surgical instrument 10 are forced apart. In other words, for the purpose of actuating the surgical instrument 10, it is necessary to overcome (at least) the spring force of the spring mechanism.

When the surgical instrument 10 is actuated, the jaws 12, 14 are moved towards one another, against the spring force of the spring mechanism 22, for the purpose of producing a gripping (or clamping) force. The direction of the gripping force is indicated by the two arrows A and B.

As has already been mentioned, the surgical instrument represented in FIG. 1 combines the functions of wire-cutting, wire-bending and also wire-positioning. A wire-receiving device 24 is provided for the purpose of positioning the bent wire. A wire-bending device 26 makes it possible to bend the wire. A wire-cutting device 28 is present for the purpose of cutting said wire. These three devices 24, 26 and 28 will be explained in greater detail below with reference to FIGS. 2 to 4.

Figure 2:
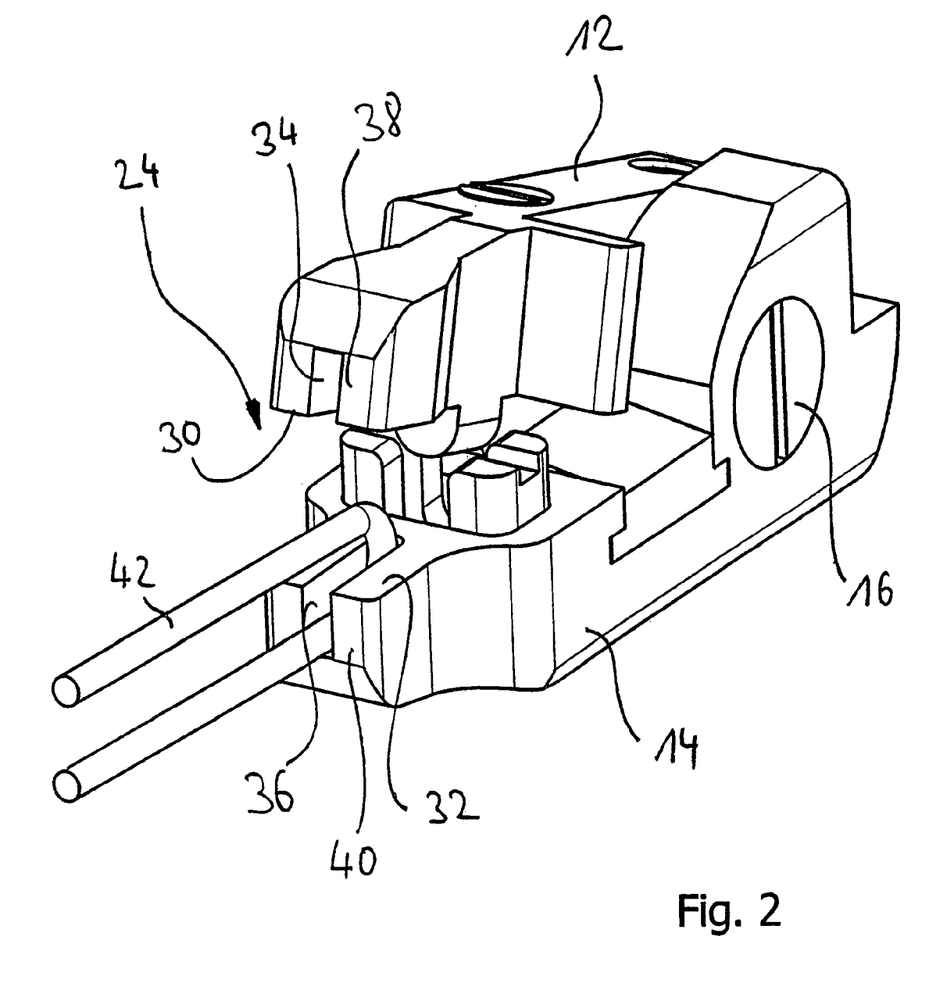
FIG. 2 shows a perspective view of the front end of the surgical instrument according to FIG. 1, with a bent wire received in a wire-receiving device.

As is represented in FIG. 2, the wire-receiving device 24 is constructed in halves, with a half in each of the two jaws 12, 14. Said two jaws 12, 14 each comprise a planar surface 30, 32. The said surfaces 30, 32 face towards one another and extend substantially perpendicularly to the direction of the gripping force (which is no longer included in the drawings in FIGS. 2 to 5). In the embodiment, the wire-receiving device 24 comprises a slot 34, 36 in each of the two jaws 12, 14. The two slots 34, 36 are aligned with one another in one plane. Each of the two slots 34, 36 is open both with respect to the surface 30, 32 of the jaw in each case and also with respect to the free end 38, 40 of the jaw in each case.

The wire-receiving device 24 in the form of the two (half-) slots 34, 36 runs substantially parallel to the direction of the gripping force. Stable positioning of a bent wire which has been received is thus guaranteed in such a way that the plane of the wire likewise extends perpendicularly to the direction of gripping force. In a departure from the embodiment represented in FIG. 2, the slots 34, 36 could also open laterally with respect to the two jaws 12, 14.

As also emerges from FIG. 2, the depth (i.e. the extension in the direction of gripping force) of each of the two slots 34, 36 approximately corresponds to the radius of bending of the wire 42 which is represented, by way of an example, in FIG. 2 and which is bent in the shape of a U. Each of the two slots 34, 36 may possess a depth which is constant along its extension or a varying depth. The choice of the profile of each slot 34, 36 in terms of depth (also) depends on the intended purpose of the wire-receiving device 24. If, for example, said wire-receiving device 24 is intended to orientate the two ends of the wire 42, which is bent in the shape of a U, parallel to one another (with substantially closed jaws 12, 14), it is expedient if each of the two slots has a depth which remains substantially the same or which varies only slightly in the direction of the free ends 38, 40 of the jaws. If, on the other hand, the distance of the two ends of the wire 42 from one another is to be variable by means of the instrument 10, it is advantageous to select the depth of at least one of the two slots 38, 40 to be smaller at least in the region of the free ends 38, 40 of the jaws than in the rearward region of the slot. If the profile in terms of depth is designed in such a way, the two ends of the wire are moved towards one another as a result of actuation of the instrument 10. On the other hand, opening of the jaws 12, 14 which are almost closed causes the two ends of the wire to move away from one another again because of the spring action inherent in the bent wire.

In a departure from the embodiment represented in FIG. 2, it would be possible to provide a slot in only one of the two jaws and to leave the surface of the other jaw completely planar, or else to provide for some other design of the surface of the jaws, according to the field of application. If only one of the two jaws is provided with a wire-receiving device in the form of a slot, it is expedient to choose the depth of the slot to be slightly greater than the radius of bending. This facilitates stable positioning of the wire in a plane parallel to the direction of gripping force.

Figure 3:
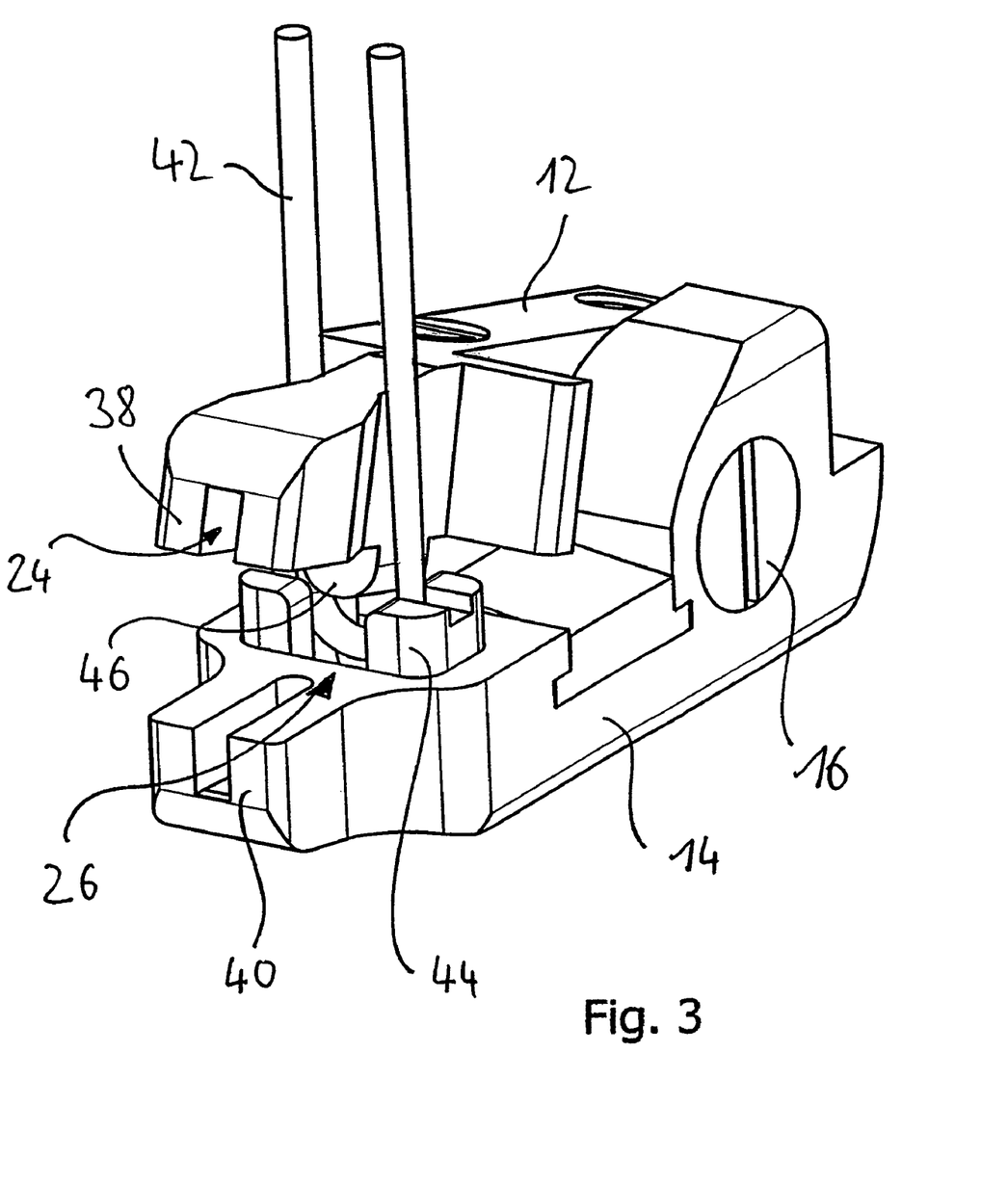
FIG. 3 shows a perspective view of the front end of the surgical instrument according to FIG. 1, with a bent wire received in a wire-bending device.

FIG. 3 shows the wire-bending device 26 of the instrument 10 in an operating position. Said wire-bending device 26 possesses a bending die 44 which is provided in a region of the lower jaw 14, and also a bending ram 46 which is provided in a region of the upper jaw 12. The wire-bending device 26 is disposed behind the wire-receiving device 24, with respect to the free ends 38, 40 of the two jaws 12, 14.

In the embodiment according to FIG. 3, the wire-bending device 26 is constructed for the purpose of bending the wire 42 in the shape of a U. For this purpose, the bending die 44 and the bending ram 46 are profiled in the shape of a U. Obviously, said bending die 44 and bending ram 46 could, if necessary, also have some other profiling (for example, in the shape of a V or an L).

In the embodiment, the wire-bending device 26, which is constructed for the purpose of bending the wire 42 in the shape of a U, makes it possible for said wire 42 to have a predefined radius of bending after the bending operation. The wire-receiving device 24 is dimensioned in conformity with the said predefined radius of bending. As has already been explained above, the depth of each of the two slots which define the wire-receiving device may, for example, approximately correspond to the radius of bending.

Figure 4:
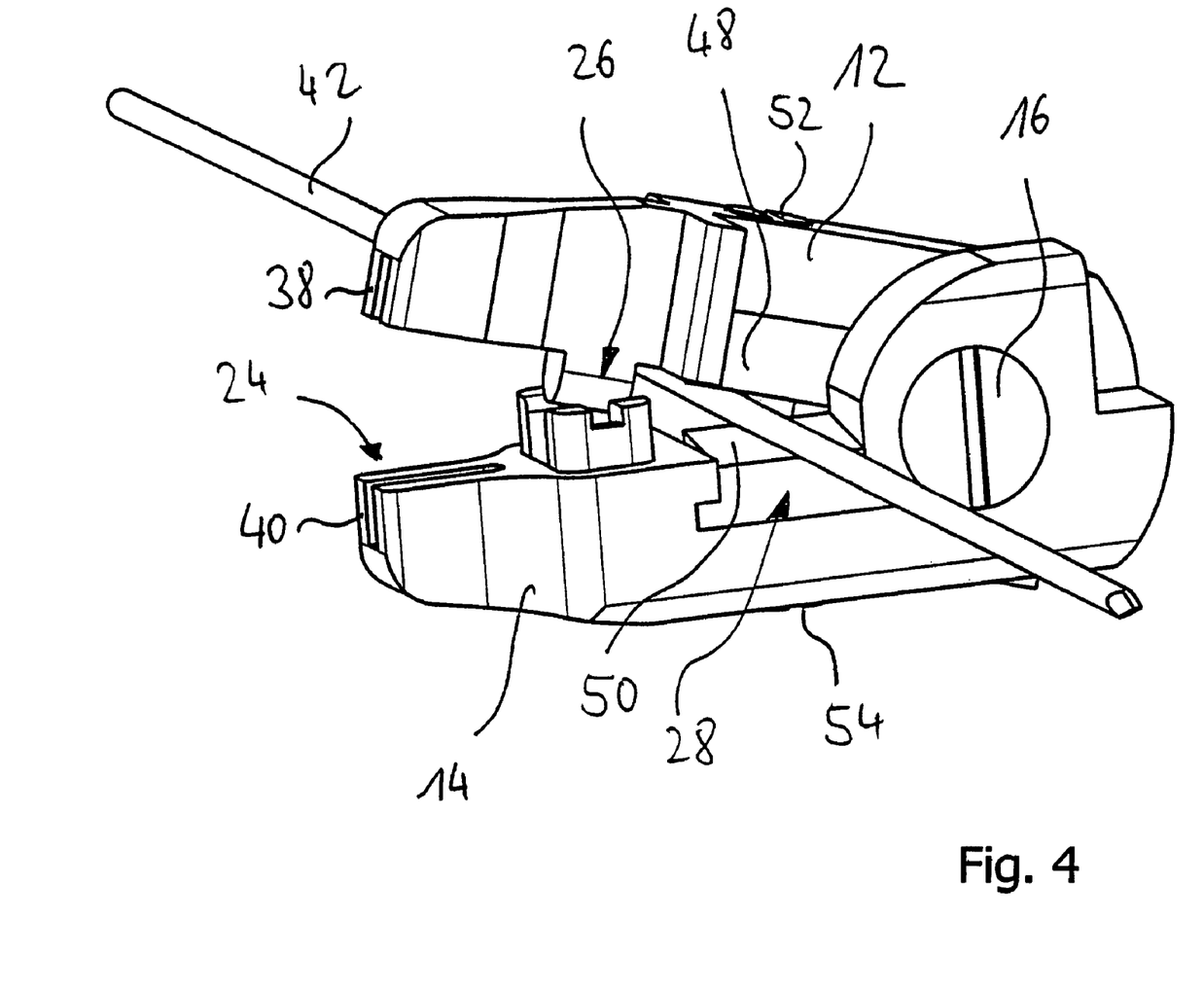
FIG. 4 shows a perspective view of the front end of the surgical instrument according to FIG. 1, with a wire received between the cutting edges of a wire-cutting device.

FIG. 4 shows an operational view of the wire-cutting device 28 of the instrument 10. As emerges from FIG. 4, said wire-cutting device comprises a first cutting edge 48 which is provided in a region of the upper jaw 12, and also a second cutting edge 50 which is provided in a region of the lower jaw 14. The two cutting edges 48, 50 are constructed as inserts (made of carbide metal, for example), which are fastened to the jaws 12, 14 by means of one or more screws 52, 54.

The wire-cutting device 28 is provided behind the wire-bending device 26 (with respect to the free ends 38, 40 of the jaws 12, 14) and close to the common bearing 16 of the jaws. Such an arrangement of the wire-cutting device 28 is advantageous since the greatest leverages can be achieved close to the bearing 16 of the jaws.

Figure 5A:
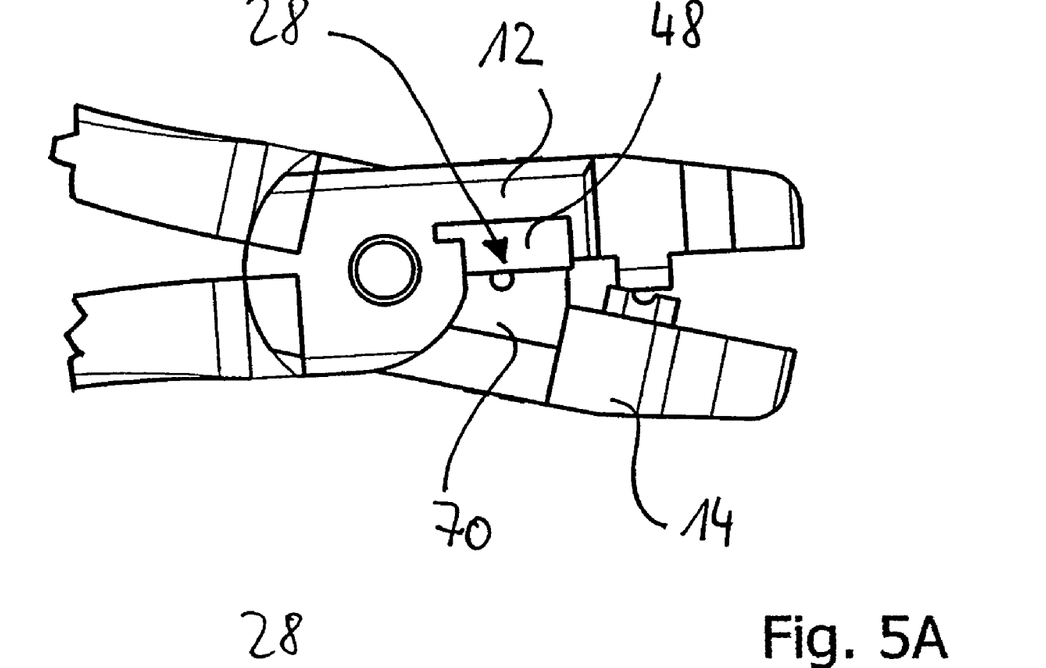
FIGS. 5A/5B each show side views, from the left and right respectively, of the front end of another surgical instrument according to the invention, with a wire-cutting device which has been modified, compared with FIG. 4.
Figure 5B:
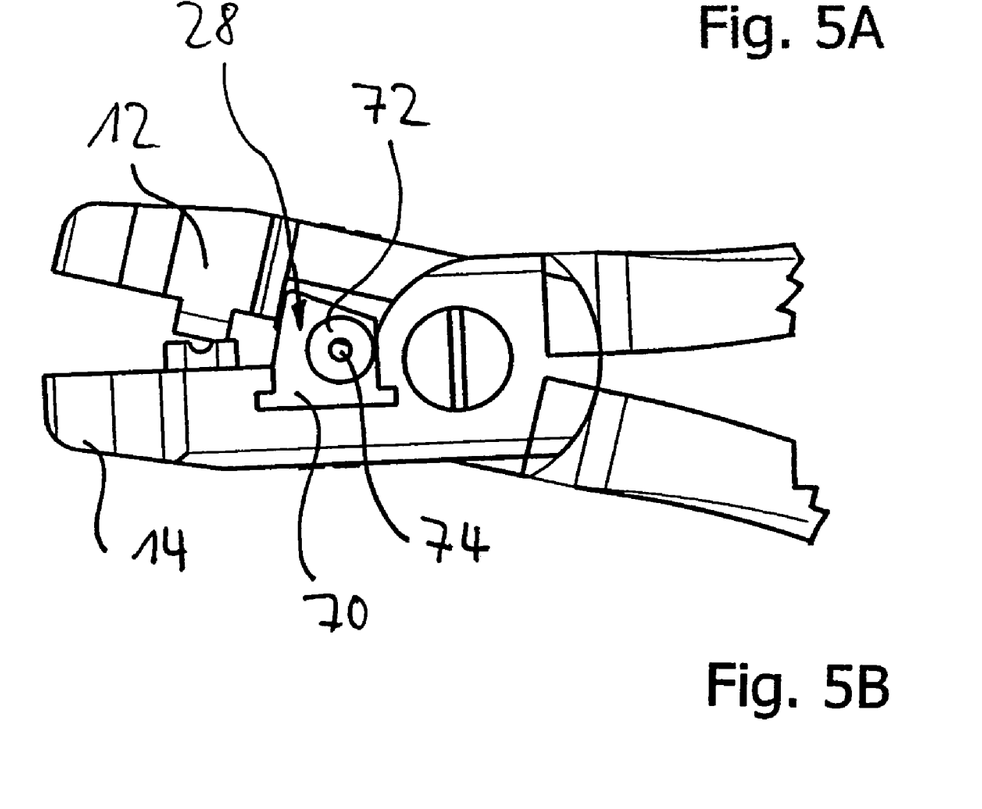

FIGS. 5A and 5B show two opposite side views of the front region of a surgical instrument according to a second embodiment. Elements which correspond have been labelled with the same reference numerals as in the first embodiment.

The surgical instrument according to the second embodiment corresponds, apart from the design of the wire-cutting device 28, to the instrument according to the first exemplified embodiment. However, in contrast to the first exemplified embodiment, the wire-cutting device 28 represented in FIGS. 5A and 5B comprises only a single cutting edge 48, which is constructed as an insert (made of carbide metal, for example) in the region of the upper jaw 12. A wire-holding device 70 is provided in the region of the lower jaw 14. Said wire-holding device 70 comprises a carbide-metal insert which extends parallel to the cutting edge 48 and has a conical depression 72 in a surface that faces away from said cutting edge 48. Said conical depression 72 opens into a circular aperture 74 into which the wire which is to be cut to length can be introduced. The wire-holding device 70 therefore fixes the wire, which has been introduced into the aperture 74, in a secure and reliable manner in position with respect to a cutting movement of the cutting edge 48. This simplifies manipulation of the instrument.

Figure 6:
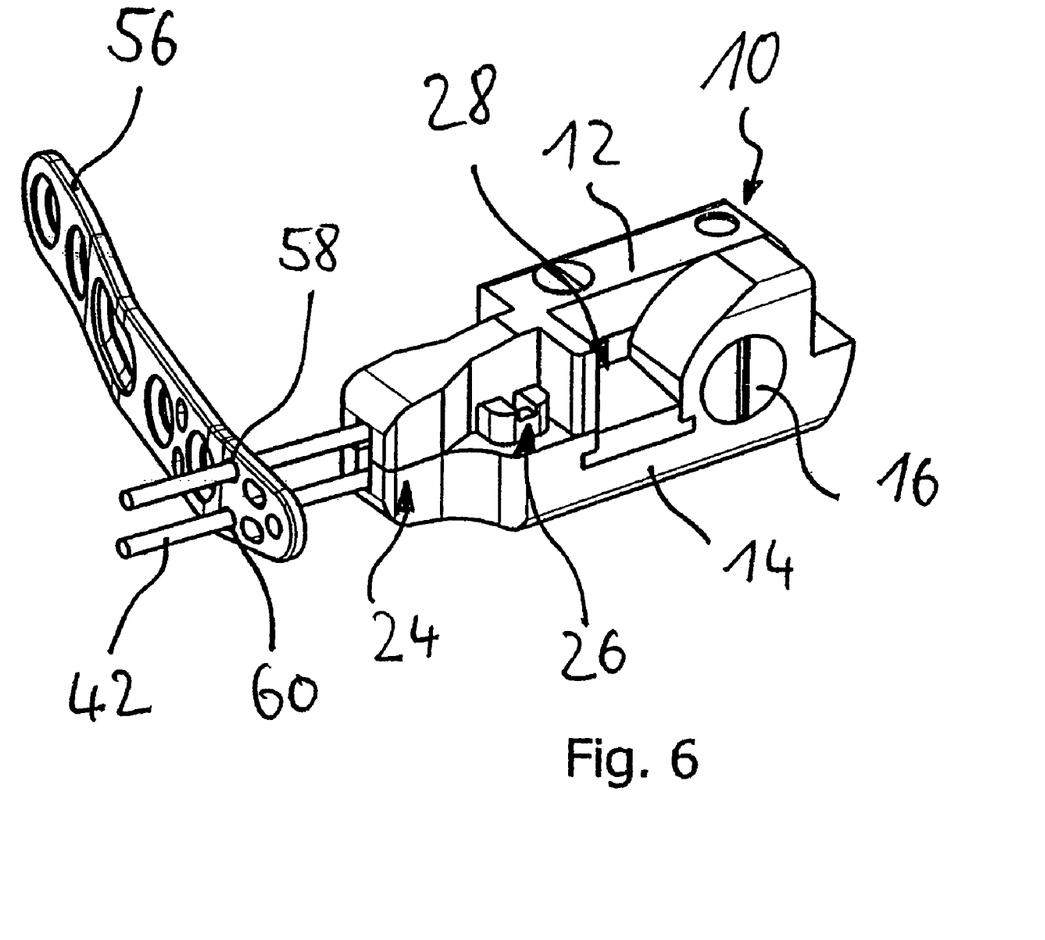
FIG. 6 shows a perspective view of a surgical system with a surgical instrument according to FIG. 1, a bone plate and also a wire which is bent in the shape of a U.

FIG. 6 shows a surgical system according to the invention, consisting of the surgical instrument according to FIGS. 1 to 4 (only part of which is represented), a wire 42 which is bent in the shape of a U by means of said instrument, and a bone plate 56. Said bone plate 56 possesses a large number of through-holes. Provided in said bone plate 56 are, inter alia, two wire-receiving apertures 58, 60. The distance of said two wire-receiving apertures 58, 60 from one another approximately amounts to twice the radius of bending of the wire 42 which has been bent in the shape of a U.

In the operating position represented in FIG. 6, the wire 42 which has been bent in the shape of a U is held in the wire-receiving device 24. The fact that the plane of the wire (which is defined by the two ends of the wire which extend parallel to one another) extends substantially parallel to the direction of the gripping force (which is not represented in FIG. 6), can be clearly seen. The wire 42 is therefore positioned in a stable manner in a plane substantially parallel to the direction of the gripping force, and can be passed through one or both of the wire-receiving apertures 58, 60 (according to the surgical requirements) by means of the instrument in a reliable manner and in a manner which is simple from the manipulation point of view.

In the case of a surgical intervention in the hand region, for example, two bores which run parallel to one another are first of all provided in the bone (and/or fragment of bone). The wire, which is initially still not bent, is then introduced through the one wire-receiving aperture 58 in the bone plate 56 and then into the bone. After that, the free end of the wire 42 is cut to length by means of the wire-cutting device 28, is bent in the shape of a U by means of the wire-bending device 26, and is then positioned in the wire-receiving device 24. The free end of the wire 42, which wire has been bent in the shape of a U and disposed in the wire-receiving device 24, is thereupon inserted, through the second wire-receiving aperture 60 in the bone plate 56, in the bore formed in the bone (and/or fragment of bone).

What is advantageous about this, for reasons connected with manipulation, is the fact that the distance between the two ends of the wire can be varied, by means of the wire-receiving device 24 which positions the wire 42, which has been bent in the shape of a U, with a plane which runs substantially parallel to the direction of gripping force, by varying the distance between the jaws 12, 14. This facilitates the threading of that end of the wire which is still free into the wire-receiving aperture 60 provided for that purpose in the bone plate 56. What is also advantageous is that three different functions (a cutting appliance, a bending appliance and a positioning aid) are combined by means of the instrument 10. This makes the surgical intervention shorter, since no change of instruments is necessary for the purpose of manipulating the wire 42. It is also possible, in advantageous manner, to match the radius of bending of the wire-bending device 26 and also the dimensioning of the wire-receiving device 24 to the distance between the two wire-receiving apertures 58, 60 in the bone plate 56.

The invention claimed is:

1. A surgical system, comprising:
   a pre-bent surgical wire having a closed end and two free ends;
   a surgical instrument for manipulating said pre-bent wire, the instrument including:
   two jaws that are movable relative to one another for generating a gripping force; and
   a wire-receiving device provided in at least one of said jaws, the wire-receiving device positioning the closed end of the pre-bent wire in a plane which is substantially parallel to a direction of the gripping force, wherein the wire-receiving device is constructed as a groove or slot, said groove or slot being provided at a free end of the respective jaw and being open in the direction of the free end of the respective jaw, said groove or slot being defined by two side walls which stabilize the location of the closed end of the pre-bent wire, each side wall extending in the plane which is substantially parallel to the direction of the gripping force; wherein both jaws are selectively operable to substantially envelop the closed end of the pre-bent wire;

a bone plate with at least two wire-receiving apertures which are spaced apart from one another to receive the two free ends of the pre-bent wire.

2. The surgical system according to claim 1, wherein the wire-receiving device is dimensioned to vary the distance between the two free ends of the pre-bent wire by actuation of the instrument when the pre-bent wire has been received.

3. The surgical system according to claim 1, wherein the instrument is constructed to enable the two free ends of the pre-bent wire, which has been received and has been previously bent in the shape of a U, to extend beyond the free end of the respective jaw.

4. The surgical system according to claim 1, wherein the wire-receiving device has dimensions which are adapted to the shape of the pre-bent wire to be received.

5. The surgical system according to claim 1, wherein the wire-receiving device is constructed in both jaws.

6. The surgical system according to claim 1, wherein the instrument further comprises a wire-bending device.

7. The surgical system according to claim 6, wherein the wire-bending device includes a bending ram constructed in a region of a first of the two jaws, and a bending die constructed in a region of a second of the two jaws.

8. The surgical system according to claim 6, wherein the wire-bending device is constructed for bending a wire in the shape of a U.

9. The surgical system according to claim 6, wherein the wire bending device is designed for achieving a predefined radius of bending.

10. The surgical system according to claim 9, wherein the wire-receiving device is dimensioned in conformity with the predefined radius of bending.

11. The surgical system according to claim 1, wherein the instrument further comprises a wire-cutting device.

12. The surgical system according to claim 11, wherein the wire-cutting device includes a cutting edge provided in a region of a first of the two jaws, and a wire-holding device provided in a region of a second of the two jaws.

13. The surgical system according to claim 12, wherein the two jaws are capable of swivelling or of translatory movement relative to one another.

14. The surgical system according to claim 1, wherein the instrument is a pair of forceps.

15. The surgical system according to claim 1, wherein the distance between the two wire-receiving apertures is selected in conformity with the dimensioning of the wire-receiving device.

16. The surgical system according to claim 15, wherein the pre-bent wire includes a radius of bending that approximately corresponds to half the distance of the two wire-receiving apertures from one another.

* * * * *